(12) United States Patent
Hillebrand et al.

(10) Patent No.: US 6,414,007 B2
(45) Date of Patent: Jul. 2, 2002

US006414007B2

(54) OXIRANYL-TRIAZOLINE THIONES AND THEIR USE AS MICROBICIDES

(75) Inventors: Stefan Hillebrand, Neuss; Manfred Jautelat, Burscheid; Astrid Mauler-Machnik, Leichlingen; Klaus Stenzel, Düsseldorf; Martin Kugler, Leichlingen; Otto Exner, Ratingen, all of (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/827,058

(22) Filed: Apr. 5, 2001

Related U.S. Application Data

(62) Division of application No. 09/529,678, filed as application No. PCT/EP98/06449 on Oct. 12, 1998, now Pat. No. 6,245,793.

(30) Foreign Application Priority Data

| | | |
|---|---|---|
| Oct. 24, 1997 | (DE) | 197 46 993 |
| May 28, 1998 | (DE) | 198 23 861 |

(51) Int. Cl.$^7$ .................... A01N 43/653; C07D 249/12
(52) U.S. Cl. .................... 514/384; 548/264.4
(58) Field of Search .................... 548/264.4; 514/384

(56) References Cited

U.S. PATENT DOCUMENTS

| | | | |
|---|---|---|---|
| 4,464,381 A | 8/1984 | Janssen et al. | 424/269 |
| 4,652,580 A | 3/1987 | Janssen et al. | 514/383 |
| 4,906,652 A | 3/1990 | Karbach et al. | 514/383 |
| 6,051,592 A | 4/2000 | Jautelat et al. | 514/384 |

FOREIGN PATENT DOCUMENTS

| | | |
|---|---|---|
| DE | 195 20 095 | 12/1996 |
| DE | 19617461 | * 11/1997 |
| EP | 0 548 025 | 6/1993 |
| WO | 87/06430 | 11/1987 |
| WO | 96/38440 | 12/1996 |

* cited by examiner

*Primary Examiner*—Patricia L. Morris
(74) *Attorney, Agent, or Firm*—Joseph C. Gil

(57) ABSTRACT

Novel oxiranyl-triazolinethiones of the formula (I)

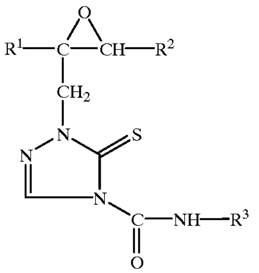

or (Ia)

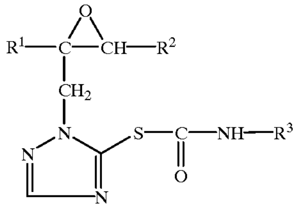

in which $R^1$, $R^2$ and $R^3$ are each as defined in the description, a process for preparing the novel substances and their use as microbicides in crop protection and in the protection of materials.

12 Claims, No Drawings

OXIRANYL-TRIAZOLINE THIONES AND THEIR USE AS MICROBICIDES

This is a Divisional Application of Ser. No. 09/529,678, filed Apr. 17, 2000, and now issued as U.S. Pat. No. 6,245,793, which is a national stage application under 35 U.S.C. 371 of PCT/EP98/06449, filed Oct. 12, 1998.

The present invention relates to novel oxiranyl-triazolinetlhiones, to a process for their preparation and to their uses as microbicides.

BACKGROUND OF THE INVENTION

It is already known that numerous azclylmethyl-oxirane derivatives have fungicidal properties (cf. EP-A 0 094 564, EP-A 0 196 038 and WO-A 96-38 440). Thus, for example, 3-(2-chloro-phenyl)-2-(4-fluoro-phenyl)-2-[(4,5-dihydro-5-thiono-1,2,4-triazol-1-yl)-methyl]-oxirane can be used for controlling fungi. The activity of this substance is good; however, it is sometimes unsatisfactory at low application rates.

SUMMMARY OF THE INVENTION

Novel oxiranyl-triazolinethiones are useful as microbicides.

DETAILED DESCRIPTION OF THE INVENTION

This invention, accordingly, provides novel oxiranyl-triazolinethiones of the formula (I)

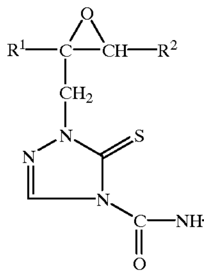

or (Ia)

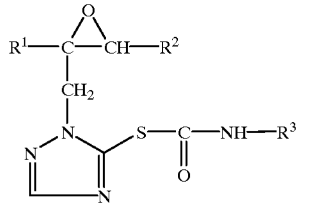

in which $R^1$ requests alkyl having 1 to 4 carbons atoms, halogenoalkyl having 1 to 4 carbon atoms and 1 to 5 halogen atoms, optionally haolgen-subsituted cycloalkyl having 3 to 7 carbon atoms, naphthyl or phenyl which is optionally mono-to trisubstituted by identical or different substituents from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, $R^2$ represents phenyl which is optionally mono- to trisubstituted by identical or different substituents from the group consisting of halogen, alkyl having 1 to 4 carbon atoms, alkoxy having1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms and $R^3$ represents alkoxyalkyl, isopropyl or n-dodecyl.

The substances according to the invention contain two asymmetrically substituted carbon atoms and can therefore be obtained in the form of diastereomers or enantiomers. The present invention relates both to the individual isomers and to their mixtures.

Furthermore, it has been found that oxiranyl-triazolinethiones of the formula (I) or (Ia) are obtained when oxirane derivatives of the formula (II)

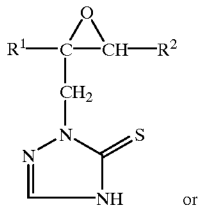

or (IIa)

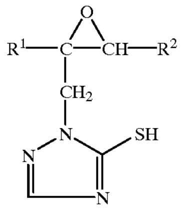

in which $R^1$ and $R^2$ are each as defined above are reacted with isocyanates of the formula $$R^3\text{—NCO} \qquad \text{(III)}$$

in which $R^3$ is as defined above, if appropriate in the presence of a catalyst and if appropriate in the presence of a diluent.

Finally, it has been found that the novel oxiranyl-triazolinethiones of the formula (I) or (Ia) have very good microbicidal properties and can be use both in crop protection and in the protection of materials for controlling undesirable microorganisms.

Surprisingly, the oxiranyl-triazolinethiones of the formula (I) or (Ia) according to the invention have better microbicidal activity, in particular fungicidal activity, than the constitutionally most similar prior-art compounds of the same direction of action Thus, the substances according to the invention surpass 3-(2-chloro-phenyl)-2-(4-fluoro-phenyl)-2-[(4,5-dihydro-5-thiono-1,2,4-triazol-1-yl)-methyl]-oxirane with respect to the fungicidal properties.

The formula (I) or (Ia) provides a general definition of the oxiranyl-triazolinethiones according to the invention.

$R^1$ preferably represents methyl, ethyl, n-propyl, isopropyl, n-butyl, sec-butyl, iso-butyl, tert-butyl, fluoro-tert-butyl, difluoro-tert-butyl, cycloalkyl having 3 to 6 carbon atoms which is optionally mono- to trisubstituted by identical or different substituents from the group consisting of fluorine, chlorine and bromine, preferably represents naphthyl or preferably represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio, $R^2$ preferably represents phenyl which may be mono- to trisubstituted by identical or different substituents from the group consisting of fluorine, chlorine, bromine, methyl, ethyl, isopropyl, tert-butyl, methoxy, ethoxy, trifluoromethyl, triclhloromethyl, difluoromethyl, difluorochloromethyl, trifluoromethoxy, difluoromethoxy and trifluoromethylthio, and $R^3$ preferably represents alkoxyalkyl having 1 to 6 carbon atoms in the alkoxy moiety and 1 to 6 carbon atoms in the alkyl moiety and also preferably represents isopropyl or n-dodecyl.

Particular preference is given to oxiranyl-triazolinethiones of the formula (I) or (Ia) in which $R^1$ represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, fluoromethyl, difluorochloromethyl, trifluoromethoxy, difluoromethoxy and trifluoromethylthio, $R^2$ represents phenyl which may be mono- to trisubstituted by identical or different substituents from the group consisting of fluorine, chlorine, bromine, methlyl, ethyl, isopropyl, tert-butyl, methoxy, ethoxy, trifluoromethyl, trichloromethyl, difluoromethyl, difluorochloromethyl, trifluoromethoxy, difluoromethoxy and trifluoromethylthio, and $R^3$ represents alkoxyalkyl having 1 to 4 carbon atoms in the alkoxy moiety and 1 to 4 carbon atoms in the alkyl moiety and also represents isopropyl or n-dodecyl.

The substituent definitions mentioned can be combined with one another at will. Moreover, individual definitions may not apply.

The oxirane derivatives required as starting materials for preparing the substances according to the invention can be present in the "thiono" form of the formula (II)

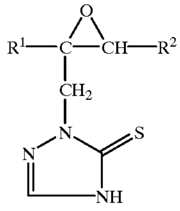

, or in the tautomeric "mercapto" form of the formula (IIa)

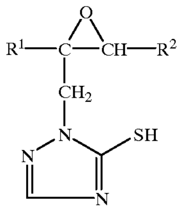

.

It is therefore possible that the substances according to the invention can be derived both from the "thiono" form of the formula (II) and from the "mercapto" form of the formula (IIa). This means that the substances according to the invention are either present as substances of the formula (I)

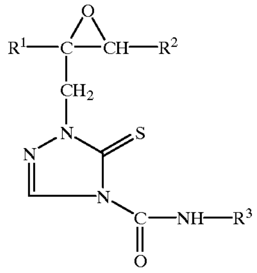

("thiono" form)

or of the formula (Ia)

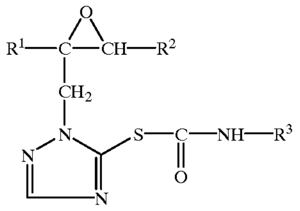

("mercapto" form)

or as mixtures of the formulae (I) and (Ia).

Examples of substances according to the invention which may be mentioned are the oxiranyl-triazolinethiones listed in the table below.

TABLE 1
(I)
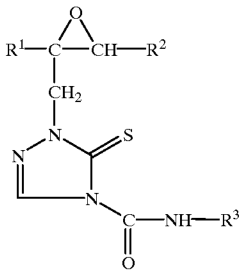
or
(Ia)
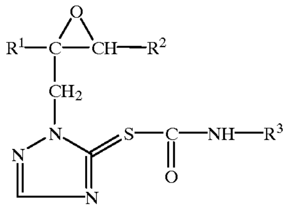
| $R^1$ | $R^2$ | $R^3$ |
|---|---|---|
| 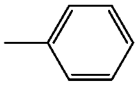 | 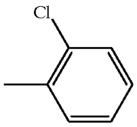 | $-CH_2-CH_2-O-CH_3$ |
| 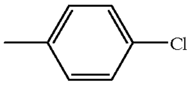 | 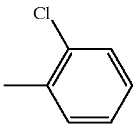 | $-CH_2-CH_2-O-CH_3$ |
| 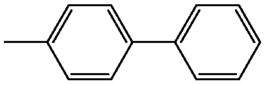 | 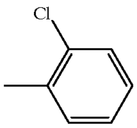 | $-CH_2-CH_2-O-CH_3$ |
| 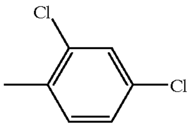 | 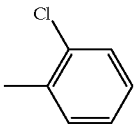 | $-CH_2-CH_2-O-CH_3$ |
| 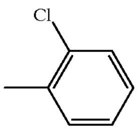 | 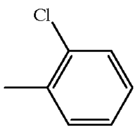 | $-CH_2-CH_2-O-CH_3$ |
| 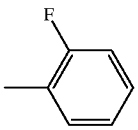 | 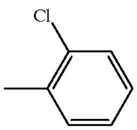 | $-CH_2-CH_2-O-CH_3$ |

TABLE 1-continued
(I)
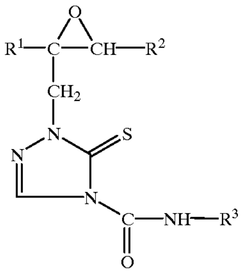
or
(Ia)
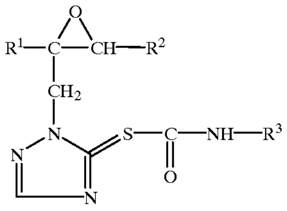
| $R^1$ | $R^2$ | $R^3$ |
|---|---|---|
| 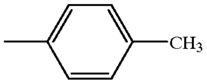 | 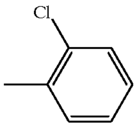 | $—CH_2—CH_2—O—CH_3$ |
| 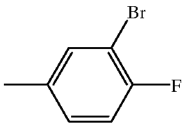 | 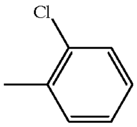 | $—CH_2—CH_2—O—CH_3$ |
| 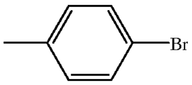 | 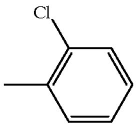 | $—CH_2—CH_2—O—CH_3$ |
| 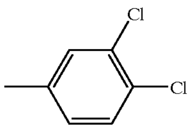 | 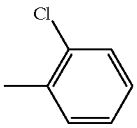 | $—CH_2—CH_2—O—CH_3$ |
| 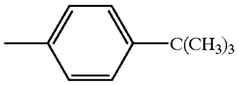 | 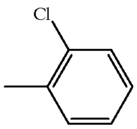 | $—CH_2—CH_2—O—CH_3$ |
| 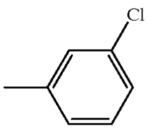 | 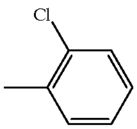 | $—CH_2—CH_2—O—CH_3$ |

TABLE 1-continued
(I)
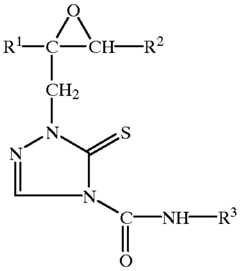
or
(Ia)
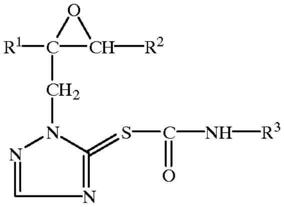
| $R^1$ | $R^2$ | $R^3$ |
| --- | --- | --- |
| 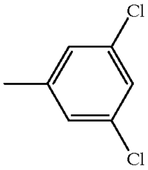 | 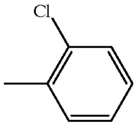 | $—CH_2—CH_2—O—CH_3$ |
| 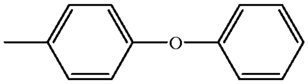 | 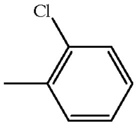 | $—CH_2—CH_2—O—CH_3$ |
| 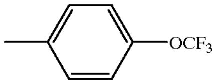 | 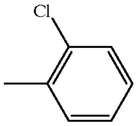 | $—CH_2—CH_2—O—CH_3$ |
| 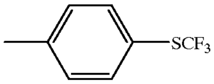 | 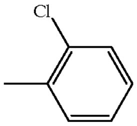 | $—CH_2—CH_2—O—CH_3$ |
| 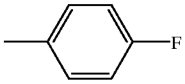 | 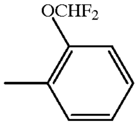 | $—CH_2—CH_2—O—CH_3$ |
| 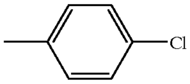 | 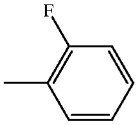 | $—CH_2—CH_2—O—CH_3$ |

TABLE 1-continued
(I)
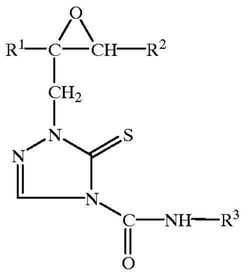
or
(Ia)
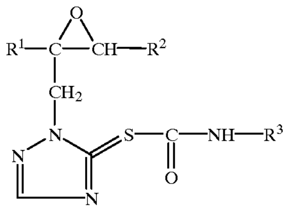
| $R^1$ | $R^2$ | $R^3$ |
|---|---|---|
| 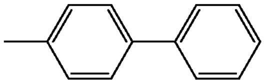 | 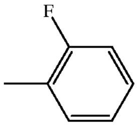 | —$CH_2$—$CH_2$—O—$CH_3$ |
| 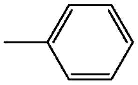 | 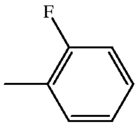 | —$CH_2$—$CH_2$—O—$CH_3$ |
| 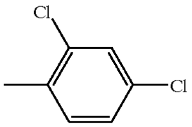 | 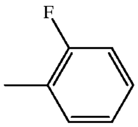 | —$CH_2$—$CH_2$—O—$CH_3$ |
| 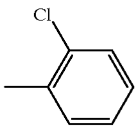 | 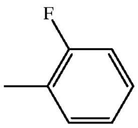 | —$CH_2$—$CH_2$—O—$CH_3$ |
| 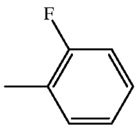 | 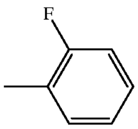 | —$CH_2$—$CH_2$—O—$CH_3$ |
| 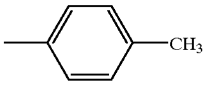 | 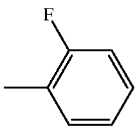 | —$CH_2$—$CH_2$—O—$CH_3$ |

TABLE 1-continued
(I)
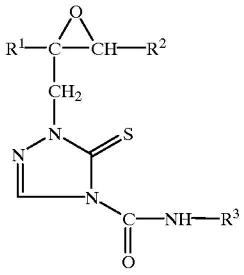
or
(Ia)
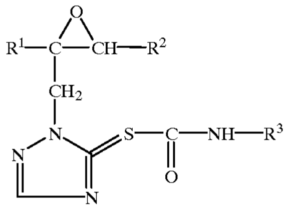
| $R^1$ | $R^2$ | $R^3$ |
|---|---|---|
| 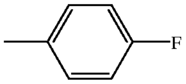 | 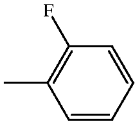 | $—CH_2—CH_2—O—C_2H_5$ |
| 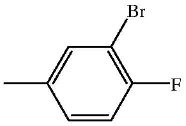 | 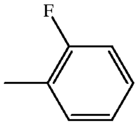 | $—CH_2—CH_2—O—CH_3$ |
| 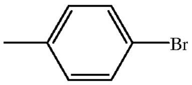 | 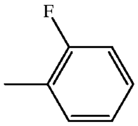 | $—CH_2—CH_2—O—CH_3$ |
| 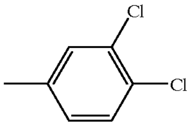 | 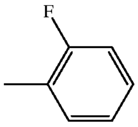 | $—CH_2—CH_2—O—CH_3$ |
| 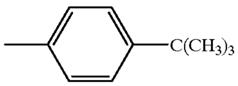 | 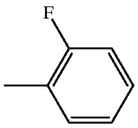 | $—CH_2—CH_2—O—CH_3$ |
| 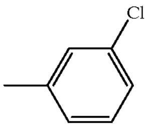 | 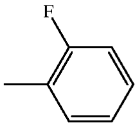 | $—CH_2—CH_2—O—CH_3$ |

TABLE 1-continued
(I)
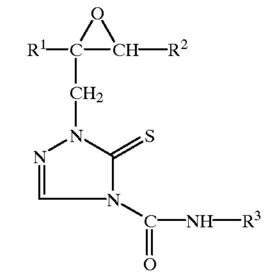
or
(Ia)
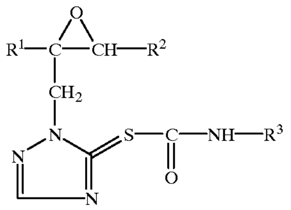
| $R^1$ | $R^2$ | $R^3$ |
|---|---|---|
| 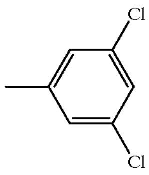 | 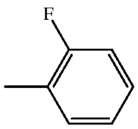 | $-CH_2-CH_2-O-CH_3$ |
| 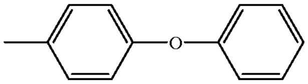 | 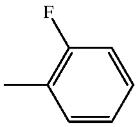 | $-CH_2-CH_2-O-CH_3$ |
| 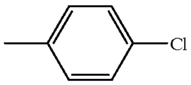 | 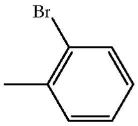 | $-CH_2-CH_2-O-CH_3$ |
| 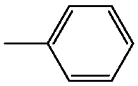 | 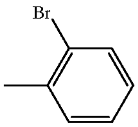 | $-CH_2-CH_2-O-CH_3$ |
| 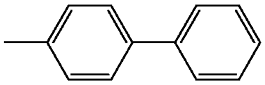 | 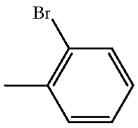 | $-CH_2-CH_2-O-CH_3$ |
| 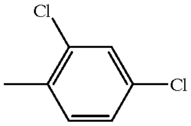 | 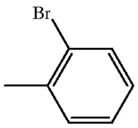 | $-CH_2-CH_2-O-CH_3$ |

TABLE 1-continued
(I)
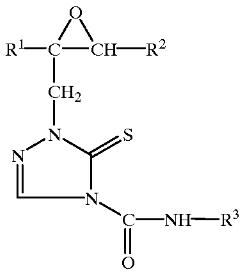
or
(Ia)
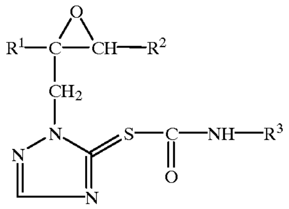
| $R^1$ | $R^2$ | $R^3$ |
|---|---|---|
| 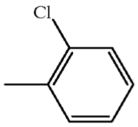 | 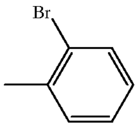 | $—CH_2—CH_2—O—CH_3$ |
| 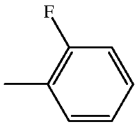 | 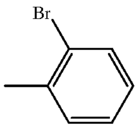 | $—CH_2—CH_2—O—CH_3$ |
| 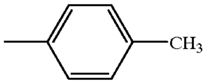 | 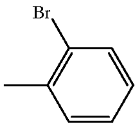 | $—CH_2—CH_2—O—CH_3$ |
| 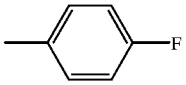 | 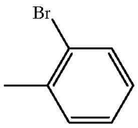 | $—CH_2—CH_2—O—CH_3$ |
| 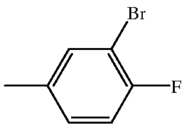 | 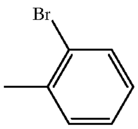 | $—CH_2—CH_2—O—CH_3$ |
| 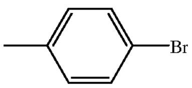 | 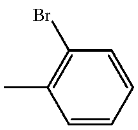 | $—CH_2—CH_2—O—CH_3$ |

TABLE 1-continued
(I)
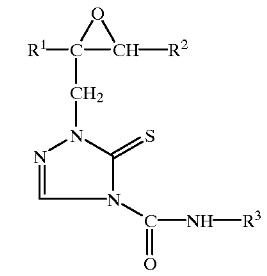
or
(Ia)
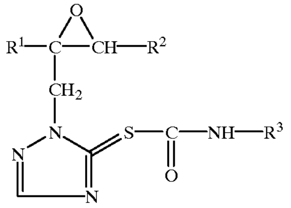
| $R^1$ | $R^2$ | $R^3$ |
|---|---|---|
| 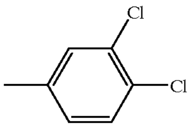 | 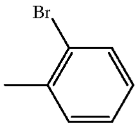 | $-CH_2-CH_2-O-CH_3$ |
| 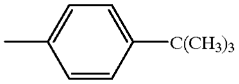 | 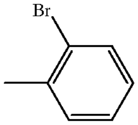 | $-CH_2-CH_2-O-CH_3$ |
| 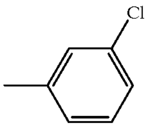 | 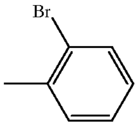 | $-CH_2-CH_2-O-CH_3$ |
| 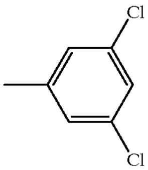 | 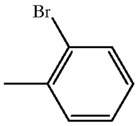 | $-CH_2-CH_2-O-CH_3$ |
| 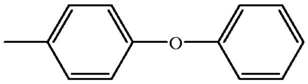 | 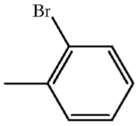 | $-CH_2-CH_2-O-CH_3$ |
| 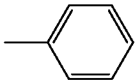 | 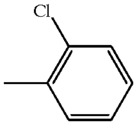 | $-(CH_2)_3-O-C_2H_5$ |

TABLE 1-continued
(I)
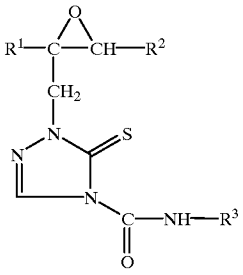
or
(Ia)
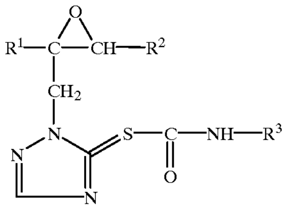
| $R^1$ | $R^2$ | $R^3$ |
|---|---|---|
| 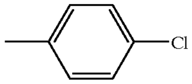 | 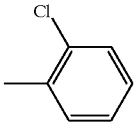 | $-(CH_2)_3-O-C_2H_5$ |
| 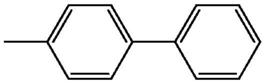 | 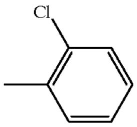 | $-(CH_2)_3-O-C_2H_5$ |
| 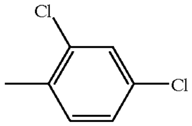 | 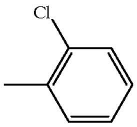 | $-(CH_2)_3-O-C_2H_5$ |
| 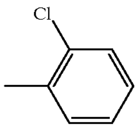 | 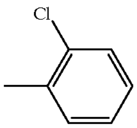 | $-(CH_2)_3-O-C_2H_5$ |
| 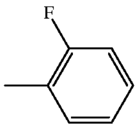 | 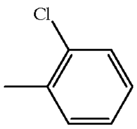 | $-(CH_2)_3-O-C_2H_5$ |
| 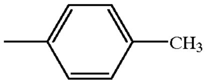 | 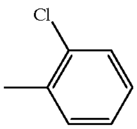 | $-(CH_2)_3-O-C_2H_5$ |

TABLE 1-continued
(I)
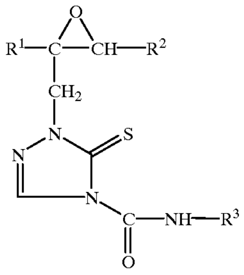
or
(Ia)
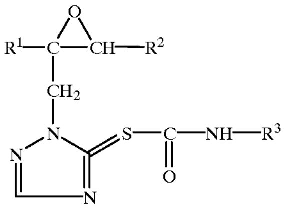
| $R^1$ | $R^2$ | $R^3$ |
|---|---|---|
| 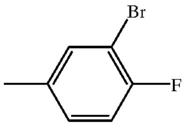 | 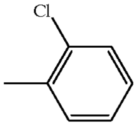 | $-(CH_2)_3-O-C_2H_5$ |
| 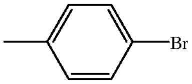 | 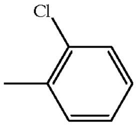 | $-(CH_2)_3-O-C_2H_5$ |
| 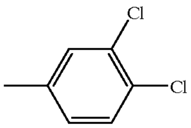 | 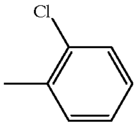 | $-(CH_2)_3-O-C_2H_5$ |
| 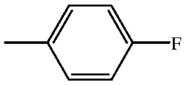 | 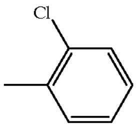 | $-(CH_2)_3-O-CH_3$ |
| 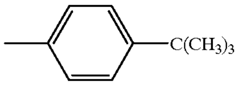 | 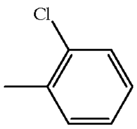 | $-(CH_2)_3-O-C_2H_5$ |
| 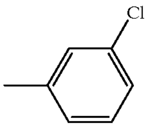 | 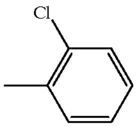 | $-(CH_2)_3-O-C_2H_5$ |

TABLE 1-continued
(I)
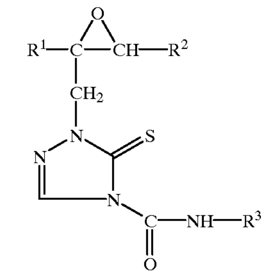
or
(Ia)
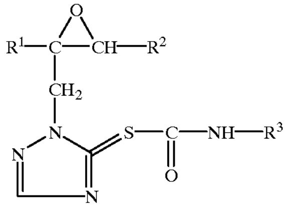
| $R^1$ | $R^2$ | $R^3$ |
|---|---|---|
| 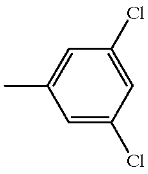 | 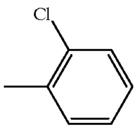 | $—(CH_2)_3—O—C_2H_5$ |
| 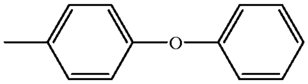 | 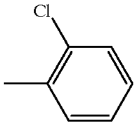 | $—(CH_2)_3—O—C_2H_5$ |
| 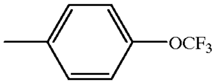 | 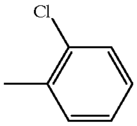 | $—(CH_2)_3—O—C_2H_5$ |
| 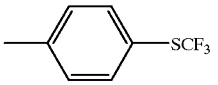 | 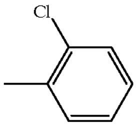 | $—(CH_2)_3—O—C_2H_5$ |
| 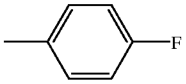 | 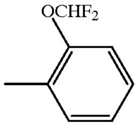 | $—(CH_2)_3—O—C_2H_5$ |
| 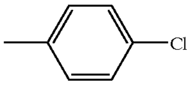 | 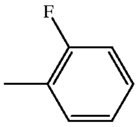 | $—(CH_2)_3—O—C_2H_5$ |

TABLE 1-continued
(I)
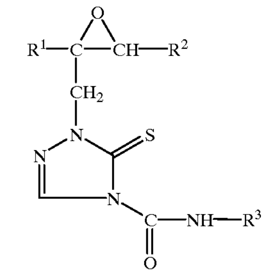
or
(Ia)
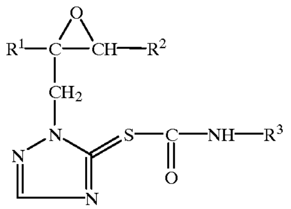
| $R^1$ | $R^2$ | $R^3$ |
|---|---|---|
| 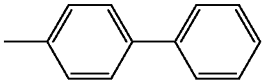 | 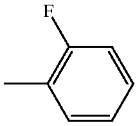 | $-(CH_2)_3-O-C_2H_5$ |
| 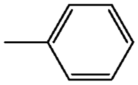 | 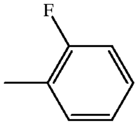 | $-(CH_2)_3-O-C_2H_5$ |
| 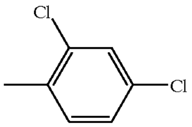 | 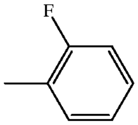 | $-(CH_2)_3-O-C_2H_5$ |
| 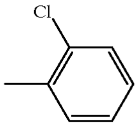 | 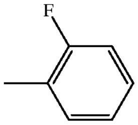 | $-(CH_2)_3-O-C_2H_5$ |
| 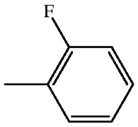 | 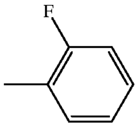 | $-(CH_2)_3-O-C_2H_5$ |
| 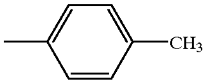 | 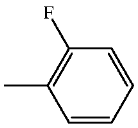 | $-(CH_2)_3-O-C_2H_5$ |

TABLE 1-continued
(I)
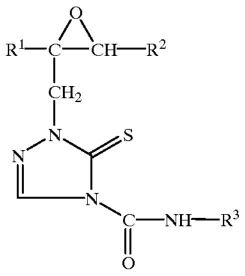
or
(Ia)
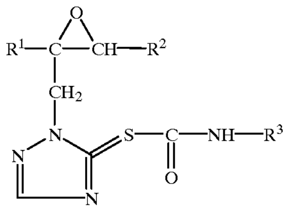
| $R^1$ | $R^2$ | $R^3$ |
|---|---|---|
| 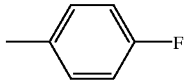 | 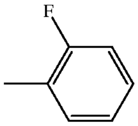 | $-(CH_2)_3-O-C_2H_5$ |
| 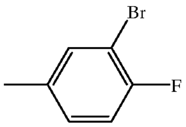 | 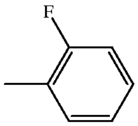 | $-(CH_2)_3-O-C_2H_5$ |
| 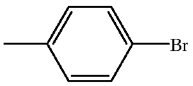 | 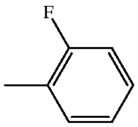 | $-(CH_2)_3-O-C_2H_5$ |
| 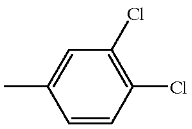 | 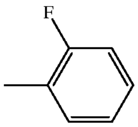 | $-(CH_2)_3-O-C_2H_5$ |
| 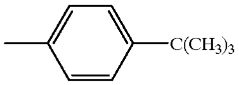 | 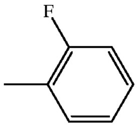 | $-(CH_2)_3-O-C_2H_5$ |
| 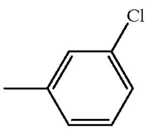 | 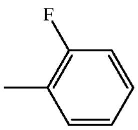 | $-(CH_2)_3-O-C_2H_5$ |

TABLE 1-continued
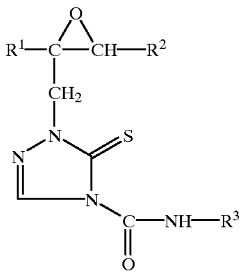
(I)
or
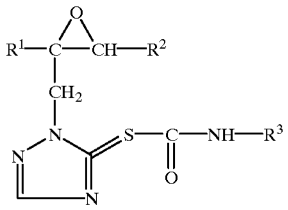
(Ia)
| $R^1$ | $R^2$ | $R^3$ |
|---|---|---|
| 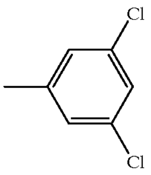 | 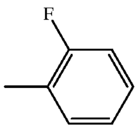 | $-(CH_2)_3-O-C_2H_5$ |
| 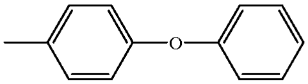 | 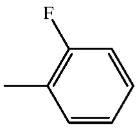 | $-(CH_2)_3-O-C_2H_5$ |
| 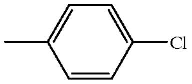 | 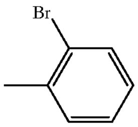 | $-(CH_2)_3-O-C_2H_5$ |
| 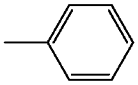 | 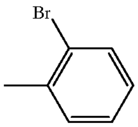 | $-(CH_2)_3-O-C_2H_5$ |
| 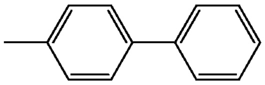 | 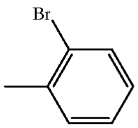 | $-(CH_2)_3-O-C_2H_5$ |
| 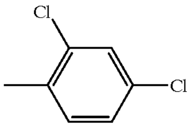 | 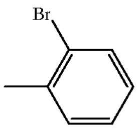 | $-(CH_2)_3-O-C_2H_5$ |

TABLE 1-continued
(I)
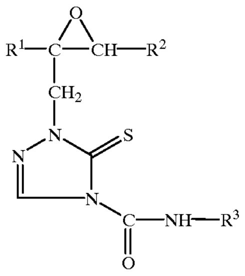
or
(Ia)
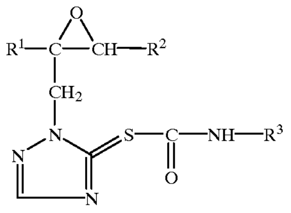
| $R^1$ | $R^2$ | $R^3$ |
|---|---|---|
| 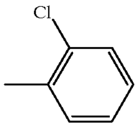 | 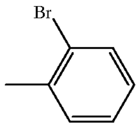 | $-(CH_2)_3-O-C_2H_5$ |
| 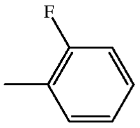 | 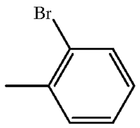 | $-(CH_2)_3-O-C_2H_5$ |
| 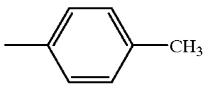 | 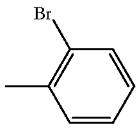 | $-(CH_2)_3-O-C_2H_5$ |
| 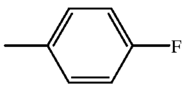 | 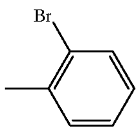 | $-(CH_2)_3-O-C_2H_5$ |
| 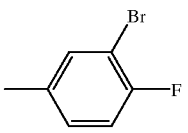 | 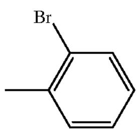 | $-(CH_2)_3-O-C_2H_5$ |
| 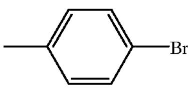 | 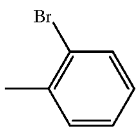 | $-(CH_2)_3-O-C_2H_5$ |

TABLE 1-continued
(I)
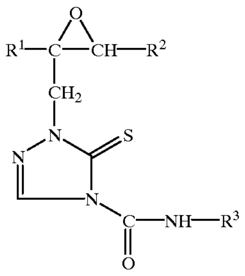
or
(Ia)
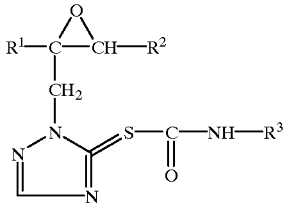
| $R^1$ | $R^2$ | $R^3$ |
|---|---|---|
| 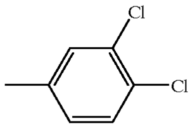 | 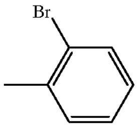 | $-(CH_2)_3-O-C_2H_5$ |
| 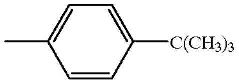 | 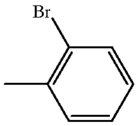 | $-(CH_2)_3-C-C_2H_5$ |
| 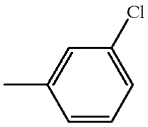 | 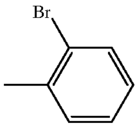 | $-(CH_2)_3-O-C_2H_5$ |
| 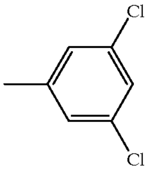 | 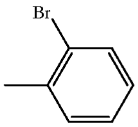 | $-(CH_2)_3-O-C_2H_5$ |
| 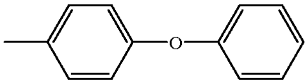 | 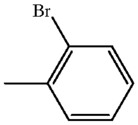 | $-(CH_2)_3-O-C_2H_5$ |

Using 3-(2-chloro-phenyl)-2-(4-fluoro-phenyl)-2-[(4,5-dihydro-5-thiono-1,2,4-triazol-1-yl)-methyl]-oxirane as starting material and 3-ethoxy-propyl isocyanate as reaction component, the course of the process according to the invention can be illustrated by the scheme below.

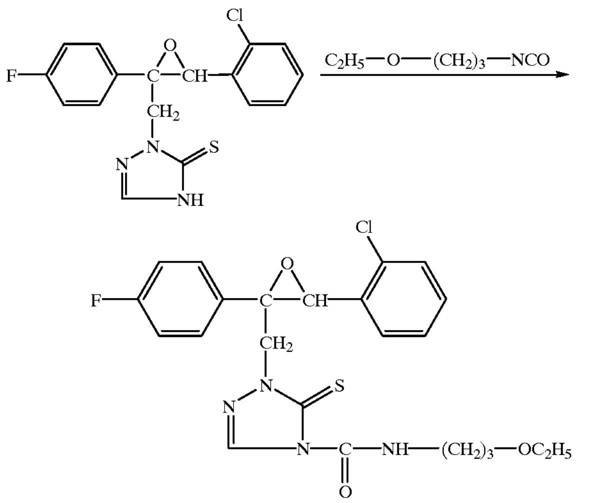

The formula (II) or (IIa) provides a general definition of the oxirane derivatives required as starting materials for carrying out the process according to the invention. In this formula, $R^1$ and $R^2$ preferably have those meanings which have already been mentioned in connection with the description of the substances of the formula (I) or (Ia) according to the invention as being preferred for these radicals.

The oxirane derivatives of the formula (II) or (IIa) are already known (cf. WO-A 96-39 440).

The formula (III) provides a general definition of the isocyanates required as reaction components for carrying out the process according to the invention. In this formula, $R^3$ preferably has those meanings which have already been mentioned in connection with the description of the substances of the formula (I) according to the invention as being preferred for this radical.

The isocyanates of the formula (III) are known or can be prepared by known methods.

Suitable catalysts for carrying out the process according to the invention are all reaction promoters which are customary for such reactions. Preference is given to using amines, such as triethylamine, pyridine, dimethylaminopyridine and diazabicyclo-undecene (DBU).

Suitable diluents for carrying out the process according to the invention are all inert organic solvents which are customary for such reactions. Preference is given to using aromatic hydrocarbons, such as toluene, xylene or decaline, also halogenated hydrocarbons, such as dichloromethane, chloroform, carbon tetrachloride, dichloroethane or trichloroethane, moreover ethers, such as diethyl ether, diisopropyl ether, methyl tert-butyl ether, methyl tert-amyl ether, dioxane or tetrahydrofuran, and furthermore nitriles, such as acetonitrile, propionitrile, n- or iso-butyronitrile.

When carrying out the process according to the invention, the reaction temperatures can be varied within a certain range. In general, the process is carried out at temperatures between −20° C. and +100° C., preferably between 0° C. and +80° C.

The process according to the invention is generally carried out under atmospheric pressure. However, it is also possible to carry out the process under elevated pressure or, if no highly volatile components are taking part in the reaction, also under reduced pressure.

When carrying out the process according to the invention, in general from 1 to 1.5 mol of isocyanate of the formula (III) and a small amount of catalyst are employed per mole of oxirane derivative of the formula (II) or (IIa). Work-up is carried out by customary methods. In general, the reaction mixture is concentrated under reduced pressure and the product that remains is freed from any impurities that may still be present by customary methods, for example by recrystallization or chromatography.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;* Pseudomonas species, such as, for example, *Pseudomonas syringae* pv. *lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Bremia species, such as, for example, *Bremia lactucae,* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Sclerotinia species, such as, for example, *Sclerotinia sclerotiorum* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Altenaria brassicae*; and Pseudocercosporella species, such as, for example, *Pseudocercosporella herpotrichoides.*

The fact that the active compounds are well tolerated by plants at the concentrations required for controlling plant diseases permits the treatment of above-ground parts of plants, of propagation stock and seeds, and of the soil.

The active compounds according to the invention can be employed in particular for controlling *Pyricularia oryzae* on rice and for controlling cereal diseases, such as Puccinia, Erysiphe and Fusarium species. Moreover, the substances according to the invention can be used successfully against Venturia, Podosphaera and Sphaerotheca. They also have very good in-vitro action.

The active compounds according to the invention may also be employed to increase the yield of crops. Moreover, they have low toxicity and are well tolerated by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or decomposed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa*, and

Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use for example organic solvents as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or, in their formulations, also mixed with known fungicides, bactericides, acaricides, nematicides or insecticides in order thus, for example, to widen the spectrum of action or to prevent development of resistance. In many cases, synergistic effects are achieved here, i.e. the activity of the mixture exceeds the activity of the individual components.

Examples of co-components in mixtures are the following compounds:

Fungicides: aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconiazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)- 1H-1,2,4-triazole-1-ethanol, α-(2,4-dichlorophenyl)-β-fluoro-b-propyl-1H-1,2,4-triazole-1-ethanol, α-(2,4-dichlorophenyl)-β-methoxy-a-methyl-1H-1,2,4-triazole-1-ethanol, α-(5-methyl-1,3-dioxan5-yl)-β-[[4-(trifluoromethyl)-phenyl]-methylene]-1H-1,2,4-triazole-1-ethanol, (5RS,6RS)-6-hydroxy-2,2,7,7-tetramethyl-5-( 1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl) oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[1-[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-aminol]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3 -[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)- 1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-1 -benzopyrane-2,1'(3'H)-isobenzofuran]-3'-one, Bactericides:

bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, *Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-regulating substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seeds of the plants can also be treated.

When using the active compounds according to the invention as fungicides, the application rates can be varied within a relatively wide range, depending on the type of application. In the treatment of parts of plants, the active compound application rates are generally between 0.1 and 10,000 g/ha, preferably between 10 and 1000 g/ha. In the treatment of seeds, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

The compositions used for protecting industrial materials generally comprise the active compounds in an amount of from 1 to 95% by weight, preferably from 10 to 75% by weight.

The use concentrations of the active compounds according to the invention depend on the species and the occurrence of the microorganisms to be controlled, and on the composition of the material to be protected. The optimum amount to be used can be determined by test series. In general, the use concentrations are in the range from 0.001 to 5% by weight, preferably from 0.05 to 1.0% by weight, based on the material to be protected.

It is possible to increase the activity and the activity spectrum of the active compounds to be used according to the invention in the protection of materials, or of the compositions, concentrates or, quite generally, formulations preparable therefrom, by adding, if appropriate, other anti-microbially active compounds, fungicides, bactericides, herbicides, insecticides or other active compounds to increase the activity spectrum or to obtain effects, such as, for example, additional protection against insects. These mixtures may have a broader activity spectrum than the compounds according to the invention.

The preparation and the use of active compounds according to the invention are illustrated by the examples below.

PREPARATION EXAMPLES

Example 1

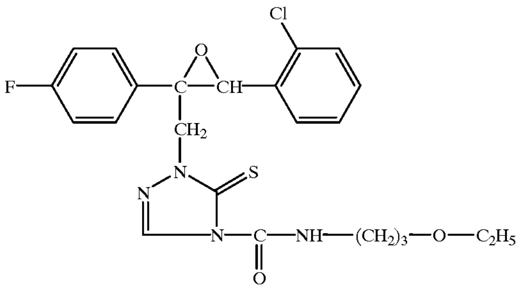

At room temperature and with stirring, a solution of 110 mg (0.97 mmol) of 3-ethoxy-propyl isocyanate in 5 ml of absolute tetrahydrofuran is added dropwise to a mixture of 350 mg (0.97 mmol) of 3-(2-chloro-phenyl)-2-(4-fluoro-phenyl)-2-[(4,5-dihydro-5-thiono-1,2,4-triazol-1-yl)-methyl]-oxirane, 0.1 ml of triethylamine and 5 ml of absolute tetrahydrofuran. After the addition has ended, the reaction mixture is heated at 60° C. for one hour and then concentrated under reduced pressure. The product that remains is chromatographed over silica gel using a mixture of cyclohexane/ethyl acetate =4:1. Concentration of the eluate gives 390 mg (82% of theory) of the substance of the formula shown above.

$^1$H-NMR spectrum (300 MHz, $CDCl_3$, TMS): δ=10.0 (s, 1H); 8.4 (s, 1H); 7.6-7.3 (m, 6H); 7.0 (t, 2H, J=8.7 Hz); 5.1 )d, 1H, J=14.9 Hz); 4.1 (s, 1H); 3.7 (d, 1H, J=14.9 Hz); 3.5-3.4 (m, 6H); 1.9-1.8 (m, 2H); 1.2 (t, 3H, J=7.0 Hz) ppm.

The compounds listed in the table below are likewise prepared by the method shown in Example 1:

TABLE 2

(I)

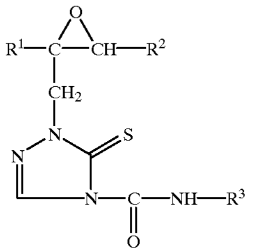

| Example No. | $R^1$ | $R^2$ | $R^3$ | Melting point in ° C. |
| --- | --- | --- | --- | --- |
| 2 | 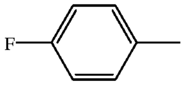 | 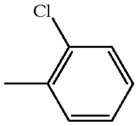 | $-CH_2-CH_2-O-CH_3$ | 105–107 |
| 3 | 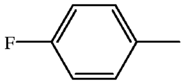 | 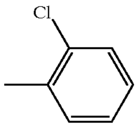 | $-CH(CH_3)_2$ | 104–106 |
| 4 | 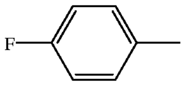 | 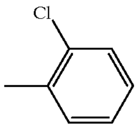 | $-C_{12}H_{25}$-n | 53–57 |
| 5 | 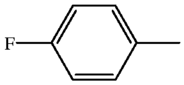 | 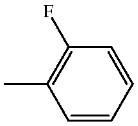 | $-CH(CH_3)_2$ | 100–101 |
| 6 | 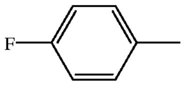 | 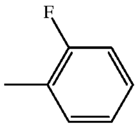 | $-CH_2-CH_2-O-CH_3$ | 96–98 |

Example 7

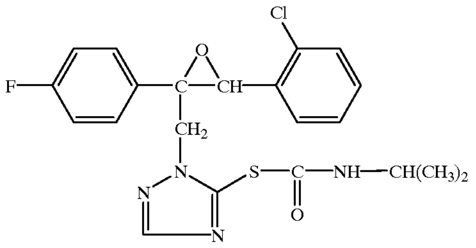

$^1$H-NMR spectrum (400 MHz, $CDCl_3$, TMS): δ=7.8 (s, 1H); 7.3-7.1 (m, 4H); 7.0-6.9 (m, 4H); 6.7 (s, 1H);5.0 (d, 1H); 4.7 (d, 1H); 4.5 (s, 1H); 3.7 (m, 1H); 1.0 (d, 6H, J=6.6 Hz) ppm.

USE EXAMPLES

Example A

Erysiphe test (barley)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp.*hordei.*

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infections are observed.

Active compounds, application rates and test results are shown in the table below.

TABLE A

Erysiphe test (barley)/protective

| Active compound | Active compound application rate g/ha | Efficacy in % |
|---|---|---|
| According to the invention: | | |
| 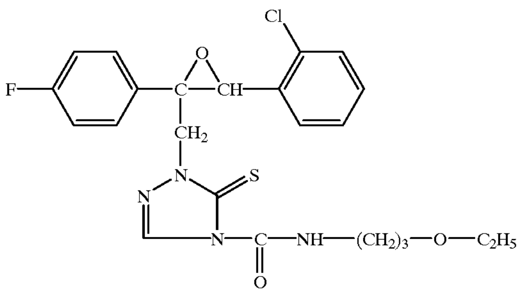 (1) | 125 | 100 |
| 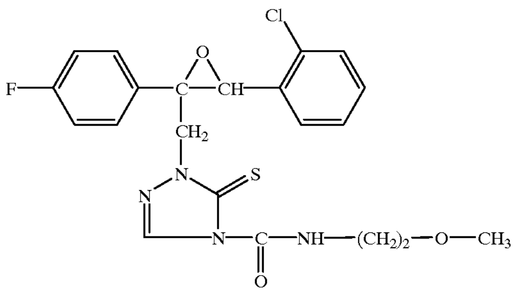 (2) | 125 | 100 |
| 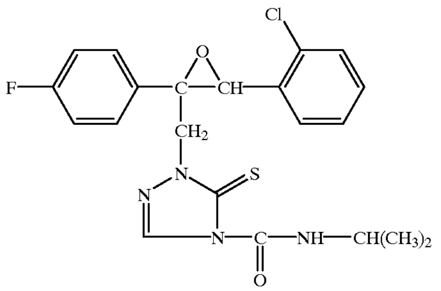 (3) | 125 | 100 |
| (4) | | |

TABLE A-continued

| Erysiphe test (barley)/protective | | |
|---|---|---|
| Active compound | Active compound application rate g/ha | Efficacy in % |
| 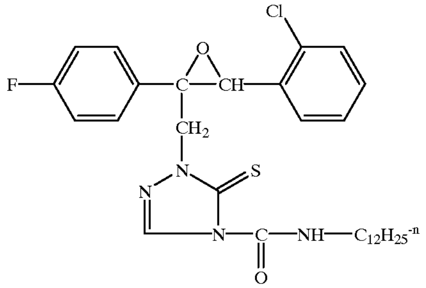 | 125 | 100 |

Example B

Erysiphe test (barley)/curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.sp. hordei.* 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infections are observed.

Active compounds, application rates and test results are shown in the table below.

TABLE B

| Erysiphe test (barley)/curative | | |
|---|---|---|
| Active compound | Active compound application rate g/ha | Efficacy in % |
| According to the invention: | | |
| (1) 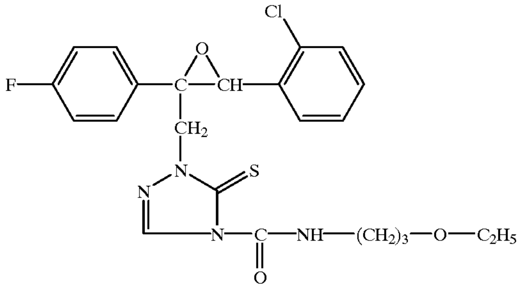 (4) | 250 | 100 |

TABLE B-continued

| Erysiphe test (barley)/curative | | |
|---|---|---|
| Active compound | Active compound application rate g/ha | Efficacy in % |
| 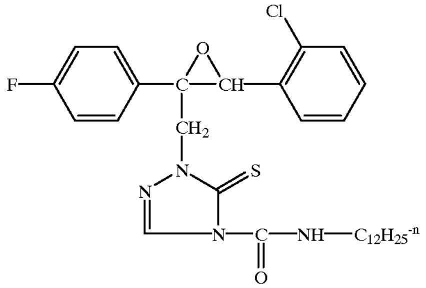 | 250 | 100 |

Example C

Erysiphe test (wheat)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *tritici.*

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infections are observed.

Active compounds, application rates and test results are shown in the table below.

TABLE C

| Erysiphe test (wheat)/protective | | |
|---|---|---|
| Active compound | Active compound application rate g/ha | Efficacy in % |
| According to the invention: | | |
| (1) 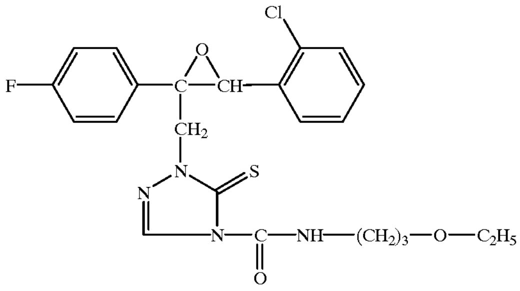 | 250 | 100 |
| (3) | | |

TABLE C-continued

Erysiphe test (wheat)/protective

| Active compound | Active compound application rate g/ha | Efficacy in % |
|---|---|---|
| 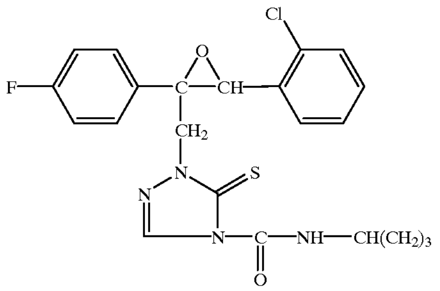 | 250 | 100 |
| (4) 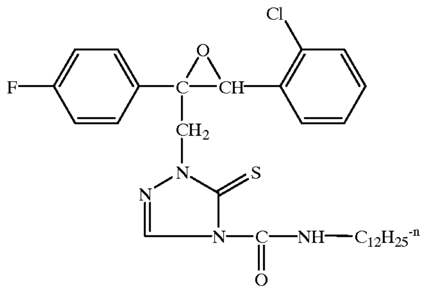 | 250 | 100 |

Example D

Leptosphaeria nodorum test (wheat)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with a spore suspension of *Leptosphaeria nodorum*. The plants remain in an incubation cabin at 20° C. and 100% relative atmospheric humidity for 48 hours.

The plants are placed in a greenhouse at a temperature of approximately 15° C. and a relative atmospheric humidity of 80%.

Evaluation is carried out 10 days after the inoculation. 0% means an efficacy which corresponds to that of the control, whereas an efficacy of 100% means that no infections are observed.

Active compounds, application rates and test results are shown in the table below.

TABLE D

| Leptosphaeria nodorum test (wheat)/protective | | | |
|---|---|---|---|
| Active compound | | Active compound application rate g/ha | Efficacy in % |
| 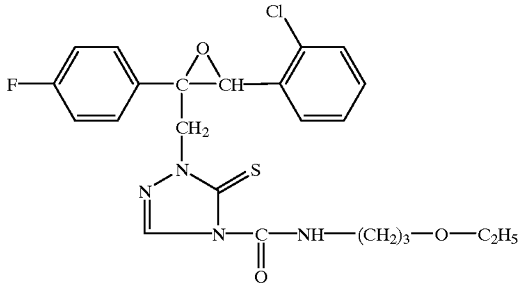 | (1) | 250 | 100 |

Example E

Puccinia test (wheat)/curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a Conidia suspension of *Puccinia recondita*. The plants remain in an incubation cabin at 20° C. and 100% relative atmospheric humidity for 48 hours. The plants are then sprayed with the preparation of active compound at the stated application rate.

The plants are placed in a greenhouse at a temperature of approximately 20° C. and a relative atmospheric humidity of approximately 80% to promote the development of rust pustules.

Evaluation is carried out 10 days after the inoculation. 0% means an efficacy which corresponds to that of the control, whereas an efficacy of 100% means that no infections are observed.

Active compounds, application rates and test results are shown in the table below.

TABLE E

| Puccinia test (wheat)/curative | | | |
|---|---|---|---|
| Active compound | | Active compound application rate g/ha | Efficacy in % |
| According to the invention: | | | |
| 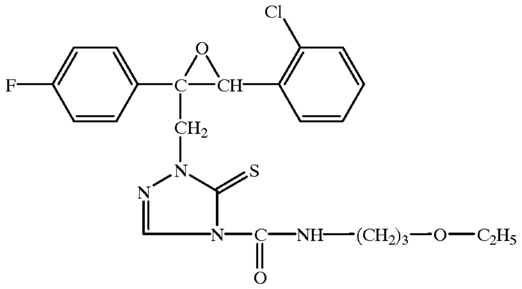 | (1) | 125 | 100 |
| | (2) | | |

TABLE E-continued

Puccinia test (wheat)/curative

| Active compound | Active compound application rate g/ha | Efficacy in % |
|---|---|---|
| 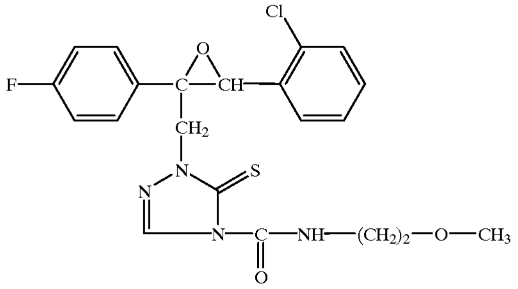 | 125 | 100 |
| (3) 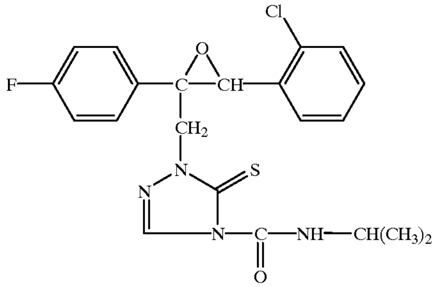 | 125 | 100 |
| (4) 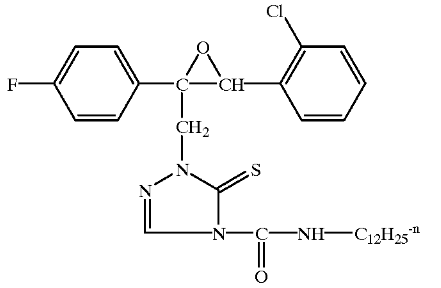 | 125 | 100 |

Example F

Puccinia test (wheat)/protective

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a Conidia 683 suspension of *Puccinia recondita*. The plants remain in an incubation cabin at 20° C. and 100% relative atmospheric humidity for 48 hours.

The plants are placed in a greenhouse at a temperature of approximately 20° C. and a relative atmospheric humidity of approximately 80% to promote the development of rust pustules.

Evaluation is carried out 10 days after the inoculation. 0% means an efficacy which corresponds to that of the control, whereas an efficacy of 100% means that no infections are observed.

Active compounds, application rates and test results are shown in the table below.

TABLE F

Puccinia test (wheat)/protective

| Active compound | | Active compound application rate g/ha | Efficacy in % |
|---|---|---|---|
| According to the invention: | | | |
| 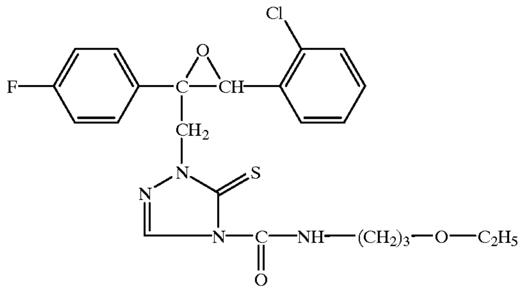 | (1) | 125 | 100 |
| 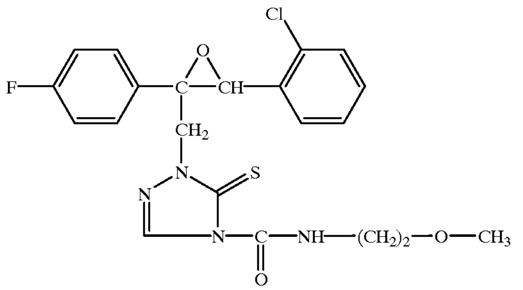 | (2) | 125 | 100 |
| 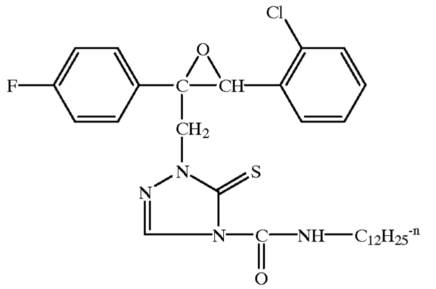 | (4) | 125 | 100 |

Example G

Podosphaera test (apple)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at approximately 23° C. and a relative atmospheric humidity of approximately 70%.

Evaluation was carried out 10 days after the inoculation. 0% means an efficacy which corresponds to that of the control, whereas an efficacy of 100% means that no infections are observed.

Active compounds, application rates and test results are shown in the table below.

TABLE G
| Podosphaera test (apple)/protective | | |
| --- | --- | --- |
| Active compound | Active compound application rate g/ha | Efficacy in % |
| Known from WO-A 96-38440: | | |
| 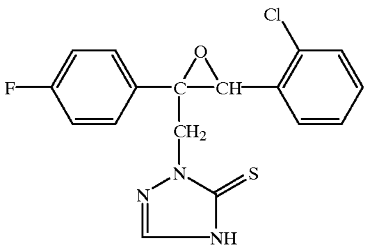 | (A) | |
| | 10 | 92 |
| | 1 | 57 |
| According to the invention: | | |
| 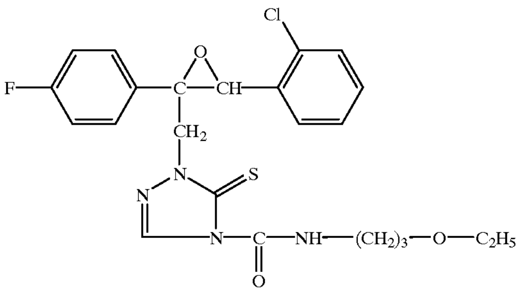 | (1) | |
| | 10 | 100 |
| | 1 | 65 |
| 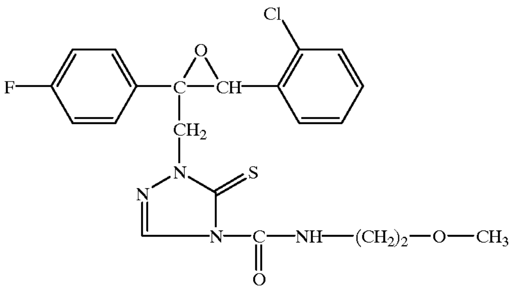 | (2) | |
| | 10 | 100 |
| | 1 | 88 |
| 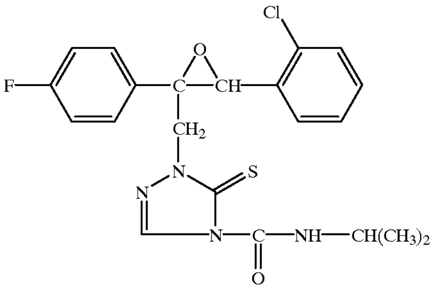 | (3) | |
| | 10 | 100 |
| | 1 | 80 |
| | (4) | |

TABLE G-continued

| Podosphaera test (apple)/protective | | |
|---|---|---|
| Active compound | Active compound application rate g/ha | Efficacy in % |
| 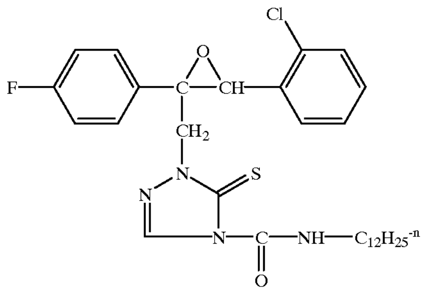 | 10 | 100 |

Example H

Inhibition test on giant colonies of Basidiomycetes

Solvent: Dimethylsulphoxide

To produce a suitable preparation of active compound, 0.2 parts by weight of active compound are admixed to 99.8 parts by weight of the abovementioned solvent.

An agar, prepared by using malt extract peptone, is mixed in a liquid state with the preparation of active compound at the particular desired application rate. After solidification, the resultant nutrient medium is incubated at 26° C. with mycelium pieces punched out of colonies of *Coriolus versicolor.*

Evaluation is carried out after 3 or 7 days' storage at 26° C. by measuring the growth of the mycelium and scoring the resulting inhibition in percent in comparison to the untreated control. 0% means an inhibition of growth which corresponds to that of the untreated control, while an inhibition of growth of 100% means that no growth of mycelium is observed.

Active compounds, active compound concentrations and test results are shown in the table below.

TABLE H

| Inhibition test on giant colonies of Basidiomycetes | | | |
|---|---|---|---|
| | Inhibition in per cent of radial growth of giant colonies at 6 ppm of active compound according to Example | | |
| Fungal species | (1) | (3) | (5) |
| Coriolus versicolor | 100 | 100 | 100 |

What is claimed is:

1. An oxiranyl-triazolinethione of the formula

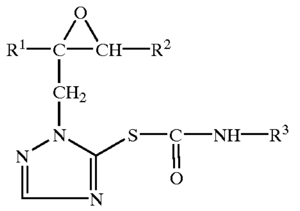

(Ia wherein $R^1$ represents alkyl having 1 to 4 carbon atoms, halogenoalkyl having 1 to 4 carbon atoms and 1 to 5 halogen atoms, optionally halogen-substituted cycloalkyl having 3 to 7 carbon atoms, naphthyl or phenyl which is optionally mono- to trisubstituted by identical or different substituents from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, $R^2$ represents phenyl which is optionally mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms and $R^3$ represents alkoxyalkyl, having 1 to 6 carbon atoms inthe alkoxy moiety and 1 to 6 carbon atoms in the alky moiety, isopropyl or n-dodecyl.

2. An oxiranyl-triazolinethione of the formula (Ia) according to claim 1 wherein $R^1$ represents methyl, ethyl, n-propyl, isopropyl, n-butyl, sec-butyl, iso-butyl, tert-butyl, fluoro-tert-butyl, difluoro-tert-butyl, cycloalkyl having three to six carbon atoms which is optionally mono- to trisubstituted by identical or different substituents from the group consisting of fluorine, chlorine and bromine, represents naphthyl or represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluoro-chloromethyl, trifluoromethoxy, difluoromethoxy and trifluoromethylthio, $R^2$ represents phenyl which may be mono- to trisubstituted by identical or different substituents from the group consisting of fluorine, chlorine, bromine, methyl, ethyl, isopropyl, tert-butyl, methoxy, ethoxy, trifluoromethyl, trichloromethyl, difluoromethyl, difluoroclhloromethyl, trifluoromethoxy, difluoromethoxy and trifluoromethylthio, and $R^3$ represents alkoxyalkyl having 1 to 6 carbon atoms in the alkoxy moiety and 1 to 6 carbon atoms in the alkyl moiety and also represents isopropyl or n-dodecyl.

3. An oxiranyl-triazolinethione according to formula (Ia) of claim 1, wherein $R^1$ represents phenyl which may be mono- to trisubstituted by identical or different substituents from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio.

4. An oxiranyl-triazolinethione according to formula (Ia) of claim 1, wherein $R^2$ represents phenyl which may be mono- to trisubstituted by identical or different substituents from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and trifluoromethylthio.

5. An oxiranyl-triazolinethione according to formula (Ia) of claim 1, wherein $R^3$ represents alkoxyalkyl having 1 to 4 carbon atoms in the alkoxy moiety and 1 to 4 carbon atoms in the alkyl moiety and also represents isoproply or n-dodecyl.

6. A microbiocidal composition comprising a microbiocidally effective amount of one or more oxiranyl-triazolinethione of the formula (Ia) according to claim 1, and an inert diluent and/or surfactant.

7. A microbiocidal composition comprising a microbiocidally effecctive amount of one or more oxiranyl-triazolinethione of the forumla (Ia) according to claim 2, and an inert diluent and/or surfactant.

8. A method for controlling undesirable microorganisms in crop protection and in the protection of materials comprising applying a microbiocidally effective amount of oxiranyl-triazolinethione of the formula (Ia) according to claim 1, to the microorganisms and/or their habitat.

9. A method for controlling undesirable microogranisms in crop protection and in the protection of materials comprising applying a microbiocidally effective amount of oxiranyl-triazolinethione of the formula (Ia) according to claim 2 to the microorganisms and/or their habitat.

10. An oxiranyl-triazolinethione according to formula (Ia) of claim 1, wherein $R^3$ represents alkoxyalkyl having 1 to 6 carbon atoms in the alkoxy moiety and 1 to 6 carbon atoms in the alkyl moiety.

11. An oxiranyl-triazolinethione according to formula (Ia) of claim 1, wherein $R^3$ represents alkoxyalkyl having 1 to 4 carbon atoms in the alkoxy moiety and 1 to 4 carbon atoms in the alkyl moiety.

12. An oxiranyl-triazolinethione according to formula (Ia) of claim 1, wherein $R^3$ represents $—CH_2—CH_2—O—CH_3$ or $—(CH_2)_3—O—C_2H_5$.

* * * * *